(12) United States Patent
Rosenberg (10) Patent No.: US 9,314,293 B2
(45) Date of Patent: Apr. 19, 2016

(54) RF ELECTRODE FOR AESTHETIC AND BODY SHAPING DEVICES AND METHOD OF USING SAME

(75) Inventor: Avner Rosenberg, Bet Shearim (IL)

(73) Assignee: SYNERON MEDICAL LTD, Yoqneam Illit (IL)

( * ) Notice: Subject to any disclaimer, the term of this patent is extended or adjusted under 35 U.S.C. 154(b) by 1518 days.

(21) Appl. No.: 12/402,936

(22) Filed: Mar. 12, 2009

(65) Prior Publication Data

US 2010/0016849 A1   Jan. 21, 2010

Related U.S. Application Data

(60) Provisional application No. 61/081,110, filed on Jul. 16, 2008.

(51) Int. Cl.
*A61F 2/00* (2006.01)
*A61B 18/14* (2006.01)
*A61N 7/00* (2006.01)
*A61B 17/00* (2006.01)
*A61B 17/30* (2006.01)
*A61B 18/00* (2006.01)

(52) U.S. Cl.
CPC . *A61B 18/14* (2013.01); *A61N 7/00* (2013.01); *A61B 2017/00057* (2013.01); *A61B 2017/00084* (2013.01); *A61B 2017/308* (2013.01); *A61B 2018/00011* (2013.01); *A61B 2018/00452* (2013.01)

(58) Field of Classification Search
USPC ............. 607/96, 98–102, 115, 148, 152, 154; 606/32, 34, 41
See application file for complete search history.

(56) References Cited

U.S. PATENT DOCUMENTS

| | | | |
|---|---|---|---|
| 1,430,354 A | 9/1922 | Burdick | |
| 2,088,780 A | 8/1937 | Follese | |
| 2,183,726 A | 2/1939 | Sommer et al. | |
| 2,231,095 A | 2/1941 | Sommer et al. | |
| 2,727,132 A | 12/1955 | Hills | |
| 2,824,308 A | 2/1958 | Duncan | |
| 3,088,205 A | 5/1963 | Ellis | |
| D196,532 S | 10/1963 | Facci | |
| 4,016,886 A | 4/1977 | Doss et al. | |
| 4,182,329 A | 1/1980 | Smit et al. | |

(Continued)

FOREIGN PATENT DOCUMENTS

| CA | 2495005 A1 | 2/2004 |
|---|---|---|
| CN | 1078383 A | 11/1993 |

(Continued)

OTHER PUBLICATIONS

Acne Clearance, LHE Clinical Casebook, Radiancy: Lighting the Future of Skin Care, © 2002.

(Continued)

*Primary Examiner* — Joseph Stoklosa
*Assistant Examiner* — Adam Avigan
(74) *Attorney, Agent, or Firm* — Smith Tempel Blaha; Gregory Scott Smith (57) ABSTRACT

A segmented RF electrode with one central segment delivering the treatment energy and at least one peripheral segment arranged around the perimeter of the central segment and a temperature control element communicating with the peripheral segment. The electrode is incorporated into an applicator for aesthetic and other skin treatments.

15 Claims, 5 Drawing Sheets

(56) References Cited

U.S. PATENT DOCUMENTS

| | | | |
|---|---|---|---|
| 4,211,230 A | 7/1980 | Woltosz | |
| 4,228,931 A | 10/1980 | Ruscitti et al. | |
| 4,321,926 A | 3/1982 | Roge | |
| D269,294 S | 6/1983 | Rakocy et al. | |
| D271,015 S | 10/1983 | Geraets | |
| D271,199 S | 11/1983 | Geraets | |
| 4,444,190 A | 4/1984 | Mutzhas | |
| D274,462 S | 6/1984 | Rakocy et al. | |
| 4,532,924 A | 8/1985 | Auth et al. | |
| 4,550,728 A | 11/1985 | Runyon et al. | |
| 4,553,936 A | 11/1985 | Wang | |
| 4,686,986 A | 8/1987 | Fenyo et al. | |
| 4,753,958 A | 6/1988 | Weinstein et al. | |
| 4,784,135 A | 11/1988 | Blum et al. | |
| 4,844,063 A | 7/1989 | Clark | |
| 4,867,682 A | 9/1989 | Hammesfahr et al. | |
| 4,869,584 A | 9/1989 | Dion | |
| 5,016,999 A | 5/1991 | Williams | |
| 5,071,418 A | 12/1991 | Rosenbaum | |
| 5,169,384 A | 12/1992 | Bosniak et al. | |
| 5,286,479 A | 2/1994 | Garlich et al. | |
| 5,316,473 A | 5/1994 | Hare | |
| 5,348,554 A | 9/1994 | Imran et al. | |
| 5,353,798 A | 10/1994 | Sieben | |
| 5,402,697 A | 4/1995 | Brooks | |
| 5,406,340 A | 4/1995 | Hoff | |
| 5,418,130 A | 5/1995 | Platz et al. | |
| 5,487,662 A | 1/1996 | Kipke et al. | |
| 5,509,916 A | 4/1996 | Taylor | |
| 5,521,392 A | 5/1996 | Kennedy et al. | |
| 5,564,851 A | 10/1996 | Connelly et al. | |
| 5,582,476 A | 12/1996 | Hansen | |
| 5,611,793 A | 3/1997 | Wilson et al. | |
| 5,628,771 A | 5/1997 | Mizukawa et al. | |
| 5,642,997 A | 7/1997 | Gregg et al. | |
| 5,658,148 A | 8/1997 | Neuberger et al. | |
| 5,693,052 A | 12/1997 | Weaver | |
| 5,698,866 A | 12/1997 | Doiron et al. | |
| 5,704,935 A | 1/1998 | Pahl et al. | |
| 5,707,403 A | 1/1998 | Grove et al. | |
| 5,722,411 A | 3/1998 | Suzuki et al. | |
| 5,731,582 A | 3/1998 | West | |
| 5,735,844 A | 4/1998 | Anderson et al. | |
| 5,755,753 A | 5/1998 | Knowlton | |
| 5,769,880 A | 6/1998 | Truckai et al. | |
| 5,814,008 A | 9/1998 | Chen et al. | |
| 5,824,023 A | 10/1998 | Anderson | |
| 5,836,999 A | 11/1998 | Eckhouse et al. | |
| 5,843,143 A | 12/1998 | Whitehurst | |
| 5,849,029 A * | 12/1998 | Eckhouse et al. | 607/104 |
| 5,868,744 A | 2/1999 | Willmen | |
| 5,871,524 A | 2/1999 | Knowlton | |
| 5,888,198 A | 3/1999 | Eggers et al. | |
| 5,919,219 A | 7/1999 | Knowlton | |
| 5,949,514 A | 9/1999 | Wargon | |
| 5,954,710 A | 9/1999 | Paolini et al. | |
| 5,961,543 A | 10/1999 | Waldmann | |
| 5,984,915 A | 11/1999 | Loeb et al. | |
| 5,993,180 A | 11/1999 | Westerhof et al. | |
| 6,024,733 A | 2/2000 | Eggers et al. | |
| 6,030,384 A | 2/2000 | Nezhat | |
| 6,053,172 A | 4/2000 | Hovda et al. | |
| 6,056,548 A | 5/2000 | Neuberger et al. | |
| 6,063,108 A | 5/2000 | Salansky et al. | |
| 6,066,134 A | 5/2000 | Eggers et al. | |
| 6,080,127 A | 6/2000 | Li et al. | |
| 6,080,391 A | 6/2000 | Tsuchiya et al. | |
| 6,081,934 A | 7/2000 | Stefanovsky et al. | |
| 6,107,326 A | 8/2000 | Jori | |
| 6,132,701 A | 10/2000 | Perez et al. | |
| 6,148,232 A | 11/2000 | Avrahami | |
| 6,186,960 B1 | 2/2001 | Tripp et al. | |
| 6,188,407 B1 | 2/2001 | Smith et al. | |
| 6,190,609 B1 | 2/2001 | Chapman et al. | |
| 6,191,110 B1 | 2/2001 | Jaynes et al. | |
| 6,210,402 B1 | 4/2001 | Olsen et al. | |
| 6,221,095 B1 | 4/2001 | Van Zuylen et al. | |
| 6,228,078 B1 | 5/2001 | Eggers et al. | |
| 6,231,571 B1 | 5/2001 | Ellman et al. | |
| 6,231,593 B1 | 5/2001 | Meserol | |
| 6,251,127 B1 | 6/2001 | Biel | |
| 6,258,319 B1 | 7/2001 | Hearst et al. | |
| 6,273,884 B1 | 8/2001 | Altshuler et al. | |
| 6,277,116 B1 | 8/2001 | Utely et al. | |
| 6,288,498 B1 | 9/2001 | Cheng | |
| 6,308,413 B1 | 10/2001 | Westerhof et al. | |
| 6,309,387 B1 | 10/2001 | Eggers et al. | |
| 6,325,797 B1 | 12/2001 | Stewart et al. | |
| 6,343,400 B1 | 2/2002 | Massholder et al. | |
| 6,343,933 B1 | 2/2002 | Montgomery et al. | |
| 6,352,535 B1 | 3/2002 | Lewis et al. | |
| 6,353,763 B1 | 3/2002 | George et al. | |
| 6,360,116 B1 | 3/2002 | Jackson et al. | |
| 6,406,157 B1 | 6/2002 | Audet | |
| 6,413,255 B1 * | 7/2002 | Stern | 606/41 |
| 6,413,268 B1 | 7/2002 | Hartman | |
| 6,425,912 B1 | 7/2002 | Knowlton | |
| 6,433,343 B1 | 8/2002 | Cimino et al. | |
| 6,436,051 B1 | 8/2002 | Morris et al. | |
| 6,461,567 B1 | 10/2002 | Hearst et al. | |
| 6,462,070 B1 | 10/2002 | Hasan et al. | |
| 6,471,716 B1 | 10/2002 | Pecukonis | |
| 6,482,204 B1 | 11/2002 | Lax et al. | |
| 6,487,447 B1 | 11/2002 | Weimann et al. | |
| 6,493,940 B2 | 12/2002 | Westerhof et al. | |
| 6,494,900 B1 | 12/2002 | Salansky et al. | |
| 6,497,702 B1 | 12/2002 | Bernaz | |
| 6,508,813 B1 | 1/2003 | Altshuler | |
| 6,511,475 B1 | 1/2003 | Altshuler et al. | |
| 6,514,243 B1 | 2/2003 | Eckhouse et al. | |
| 6,517,532 B1 | 2/2003 | Altshuler et al. | |
| 6,533,775 B1 | 3/2003 | Rizoiu et al. | |
| 6,558,653 B2 | 5/2003 | Andersen et al. | |
| 6,572,637 B1 | 6/2003 | Yamazaki et al. | |
| 6,594,905 B2 | 7/2003 | Furst et al. | |
| 6,602,245 B1 | 8/2003 | Thiberg | |
| 6,612,819 B1 | 9/2003 | Furst et al. | |
| 6,618,620 B1 | 9/2003 | Freundlich et al. | |
| 6,632,002 B1 | 10/2003 | Chubb et al. | |
| 6,637,877 B1 | 10/2003 | Hartley et al. | |
| 6,662,054 B2 | 12/2003 | Kreindel et al. | |
| 6,663,620 B2 | 12/2003 | Altshuler et al. | |
| 6,676,655 B2 | 1/2004 | McDaniel | |
| 6,702,808 B1 | 3/2004 | Kreindel | |
| 6,708,060 B1 | 3/2004 | Avrahami et al. | |
| 6,723,092 B2 | 4/2004 | Brown et al. | |
| D490,156 S | 5/2004 | Fischer et al. | |
| D490,526 S | 5/2004 | Jonsen | |
| 6,743,211 B1 | 6/2004 | Prausnitz et al. | |
| 6,758,845 B1 | 7/2004 | Weckwerth et al. | |
| 6,761,729 B2 | 7/2004 | Babaev | |
| 6,770,069 B1 | 8/2004 | Hobart et al. | |
| 6,780,838 B2 | 8/2004 | Lipton et al. | |
| 6,795,728 B2 | 9/2004 | Chornenky et al. | |
| RE38,634 E | 10/2004 | Westerhof et al. | |
| 6,887,260 B1 | 5/2005 | McDaniel | |
| 6,889,090 B2 | 5/2005 | Kreindel | |
| 6,918,907 B2 | 7/2005 | Kelly et al. | |
| 6,997,923 B2 | 2/2006 | Anderson et al. | |
| 7,006,874 B2 | 2/2006 | Knowlton et al. | |
| 7,013,179 B2 | 3/2006 | Carter et al. | |
| 7,022,121 B2 | 4/2006 | Stern et al. | |
| 7,077,840 B2 | 7/2006 | Altshuler et al. | |
| 7,115,123 B2 * | 10/2006 | Knowlton et al. | 606/41 |
| 7,115,124 B1 | 10/2006 | Xiao | |
| 7,153,298 B1 | 12/2006 | Cohen | |
| 7,204,832 B2 | 4/2007 | Altshuler et al. | |
| 7,234,239 B2 | 6/2007 | Saito et al. | |
| 7,266,414 B2 | 9/2007 | Cornelius et al. | |
| 7,275,819 B2 | 10/2007 | Bleau | |
| 7,278,991 B2 | 10/2007 | Morris et al. | |
| 7,416,550 B2 | 8/2008 | Protsenko et al. | |
| 7,601,149 B2 | 10/2009 | DiCarlo et al. | |
| 7,771,419 B2 * | 8/2010 | Carmel et al. | 606/32 |

(56) References Cited

U.S. PATENT DOCUMENTS

| | | | |
|---|---|---|---|
| 7,824,394 B2 | 11/2010 | Manstein | |
| 7,935,107 B2 | 5/2011 | Altshuler et al. | |
| 7,963,985 B2 | 6/2011 | Minamoto et al. | |
| 8,021,360 B2 * | 9/2011 | Dunning et al. | 606/32 |
| 8,109,927 B2 | 2/2012 | Kelly et al. | |
| 8,135,475 B2 | 3/2012 | Kreindel et al. | |
| 8,157,807 B2 | 4/2012 | Ferren et al. | |
| 8,202,268 B1 | 6/2012 | Wells et al. | |
| 8,206,381 B2 | 6/2012 | Lischinsky et al. | |
| 8,235,989 B2 | 8/2012 | Palanker et al. | |
| 8,409,189 B2 * | 4/2013 | Muller | 606/34 |
| 8,506,564 B2 | 8/2013 | Long et al. | |
| 2001/0007068 A1 | 7/2001 | Ota et al. | |
| 2002/0058936 A1 | 5/2002 | Avrahami et al. | |
| 2002/0104543 A1 | 8/2002 | Hollander et al. | |
| 2002/0120256 A1 | 8/2002 | Furuno et al. | |
| 2002/0120260 A1 | 8/2002 | Morris et al. | |
| 2002/0120261 A1 | 8/2002 | Morris et al. | |
| 2002/0128641 A1 | 9/2002 | Underwood et al. | |
| 2002/0143373 A1 | 10/2002 | Courtnage et al. | |
| 2002/0147384 A1 | 10/2002 | Uchikubo | |
| 2002/0183245 A1 | 12/2002 | Hasan et al. | |
| 2002/0190337 A1 | 12/2002 | House et al. | |
| 2002/0198575 A1 | 12/2002 | Sullivan | |
| 2003/0032900 A1 | 2/2003 | Ella | |
| 2003/0032950 A1 | 2/2003 | Altshuler et al. | |
| 2003/0055414 A1 | 3/2003 | Altshuler et al. | |
| 2003/0097162 A1 | 5/2003 | Kreindel | |
| 2003/0109871 A1 | 6/2003 | Johnson et al. | |
| 2003/0135250 A1 | 7/2003 | Lauman et al. | |
| 2003/0139790 A1 | 7/2003 | Ingle et al. | |
| 2003/0195494 A1 | 10/2003 | Altshuler et al. | |
| 2003/0199946 A1 | 10/2003 | Gutwein | |
| 2003/0216728 A1 * | 11/2003 | Stern et al. | 606/41 |
| 2004/0010250 A1 | 1/2004 | Manna et al. | |
| 2004/0010298 A1 | 1/2004 | Altshuler et al. | |
| 2004/0064167 A1 | 4/2004 | Berry et al. | |
| 2004/0133251 A1 | 7/2004 | Altshuler et al. | |
| 2004/0143308 A1 | 7/2004 | Lundahl et al. | |
| 2004/0147984 A1 | 7/2004 | Altshuler et al. | |
| 2004/0167501 A1 | 8/2004 | Island et al. | |
| 2004/0181216 A1 | 9/2004 | Kelly et al. | |
| 2004/0186466 A1 | 9/2004 | Chornenky | |
| 2004/0193234 A1 | 9/2004 | Butler | |
| 2004/0210214 A1 | 10/2004 | Knowlton | |
| 2004/0236320 A1 | 11/2004 | Protsenko et al. | |
| 2004/0260210 A1 | 12/2004 | Ella et al. | |
| 2004/0267252 A1 | 12/2004 | Washington et al. | |
| 2005/0015042 A1 | 1/2005 | Sun et al. | |
| 2005/0043653 A1 | 2/2005 | Trimmer et al. | |
| 2005/0049543 A1 | 3/2005 | Anderson et al. | |
| 2005/0075573 A1 | 4/2005 | Park et al. | |
| 2005/0137654 A1 | 6/2005 | Hoenig et al. | |
| 2005/0137655 A1 | 6/2005 | MacFarland et al. | |
| 2005/0143793 A1 | 6/2005 | Korman et al. | |
| 2005/0147137 A1 | 7/2005 | Slatkine | |
| 2005/0177139 A1 | 8/2005 | Yamazaki et al. | |
| 2005/0288680 A1 * | 12/2005 | Ingle et al. | 606/99 |
| 2006/0036300 A1 | 2/2006 | Kreindel | |
| 2006/0095096 A1 | 5/2006 | DeBenedictis et al. | |
| 2006/0149343 A1 | 7/2006 | Altshuler et al. | |
| 2006/0184024 A1 | 8/2006 | Da Silva et al. | |
| 2006/0200213 A1 | 9/2006 | McDaniel | |
| 2006/0206173 A1 | 9/2006 | Gertner et al. | |
| 2006/0224217 A1 | 10/2006 | Burgmann et al. | |
| 2006/0231568 A1 | 10/2006 | Lynn et al. | |
| 2006/0247741 A1 | 11/2006 | Hsu et al. | |
| 2006/0259102 A1 | 11/2006 | Slatkine | |
| 2006/0271028 A1 | 11/2006 | Altshuler et al. | |
| 2007/0016117 A1 | 1/2007 | Sliwa et al. | |
| 2007/0038206 A1 | 2/2007 | Altshuler et al. | |
| 2007/0093798 A1 | 4/2007 | Debenedictis et al. | |
| 2007/0106349 A1 | 5/2007 | Karni et al. | |
| 2007/0129771 A1 | 6/2007 | Kurtz et al. | |
| 2007/0142881 A1 | 6/2007 | Hennings | |
| 2007/0191821 A1 | 8/2007 | Boxer Wachler | |
| 2007/0197895 A1 | 8/2007 | Nycz et al. | |
| 2007/0198004 A1 | 8/2007 | Altshuler et al. | |
| 2007/0206275 A1 | 9/2007 | Hemmer et al. | |
| 2007/0213696 A1 | 9/2007 | Altshuler et al. | |
| 2007/0239142 A1 | 10/2007 | Altshuler et al. | |
| 2007/0239143 A1 | 10/2007 | Altshuler et al. | |
| 2007/0271714 A1 | 11/2007 | Adam et al. | |
| 2008/0051680 A1 | 2/2008 | Luebcke | |
| 2008/0071334 A1 | 3/2008 | Hoenig et al. | |
| 2008/0082090 A1 | 4/2008 | Manstein | |
| 2008/0123238 A1 | 5/2008 | Campos et al. | |
| 2008/0125658 A1 | 5/2008 | Lee et al. | |
| 2008/0139901 A1 | 6/2008 | Altshuler et al. | |
| 2008/0154247 A1 | 6/2008 | Dallarosa et al. | |
| 2008/0183167 A1 | 7/2008 | Britva et al. | |
| 2008/0195091 A1 * | 8/2008 | Takashino et al. | 606/41 |
| 2008/0215124 A1 | 9/2008 | Wagenaar et al. | |
| 2008/0221504 A1 | 9/2008 | Aghion | |
| 2008/0294153 A1 | 11/2008 | Allshuler et al. | |
| 2008/0306476 A1 | 12/2008 | Hennings et al. | |
| 2009/0036953 A1 | 2/2009 | Gustavsson | |
| 2009/0043293 A1 | 2/2009 | Pankratov et al. | |
| 2009/0112205 A1 | 4/2009 | McGill et al. | |
| 2009/0119834 A1 | 5/2009 | Kneale et al. | |
| 2009/0149930 A1 * | 6/2009 | Schenck | 607/100 |
| 2009/0171341 A1 * | 7/2009 | Pope et al. | 606/34 |
| 2009/0182315 A1 | 7/2009 | Zigan et al. | |
| 2009/0192503 A1 | 7/2009 | Epshtein et al. | |
| 2009/0234341 A1 | 9/2009 | Roth | |
| 2009/0234342 A1 | 9/2009 | Ely et al. | |
| 2009/0240310 A1 | 9/2009 | Kennedy | |
| 2009/0299361 A1 | 12/2009 | Flyash et al. | |
| 2010/0063565 A1 | 3/2010 | Beerwerth et al. | |
| 2010/0185193 A1 | 7/2010 | Kreindel | |
| 2010/0185194 A1 | 7/2010 | Kreindel | |
| 2010/0198134 A1 | 8/2010 | Eckhouse | |
| 2010/0274329 A1 | 10/2010 | Bradley et al. | |
| 2011/0112405 A1 | 5/2011 | Barthe et al. | |
| 2011/0137386 A1 | 6/2011 | Kreindel | |
| 2011/0166559 A1 | 7/2011 | Eckhouse et al. | |
| 2011/0196363 A1 | 8/2011 | Kreindel | |
| 2012/0143270 A1 | 6/2012 | Mehta | |
| 2012/0290023 A1 | 11/2012 | Boyden et al. | |
| 2013/0289679 A1 | 10/2013 | Eckhouse et al. | |

FOREIGN PATENT DOCUMENTS

| | | | |
|---|---|---|---|
| EP | 0528055 A1 | 2/1993 | |
| EP | 0743029 B1 | 7/2002 | |
| EP | 0824019 B1 | 11/2002 | |
| GB | 2125986 A | 8/1982 | |
| GB | 2202442 A | 9/1988 | |
| JP | 04299998 A2 | 10/1992 | |
| JP | 06113920 A2 | 4/1994 | |
| JP | 11132843 A2 | 12/1999 | |
| JP | 2003034630 | 2/2003 | |
| WO | WO-83/02389 A1 | 7/1983 | |
| WO | WO-93/21992 A1 | 11/1993 | |
| WO | WO-99/09143 A1 | 2/1999 | |
| WO | WO-9909143 A1 | 2/1999 | |
| WO | WO-99/34867 A1 | 7/1999 | |
| WO | WO-02/078644 A2 | 10/2002 | |
| WO | WO-02078644 A2 | 10/2002 | |
| WO | WO-03/039367 A1 | 5/2003 | |
| WO | WO-03093967 A1 | 5/2003 | |
| WO | WO-2006/128034 A1 | 11/2006 | |

OTHER PUBLICATIONS

Acne Star web page, describing "How to use get rid of Acne Treatment", printed May 5, 2005.

Acne Star web page, describing Clinical Studies, "The Treatment of acne vulgaris with a novel device that uses Gallium-Nitride diode light", printed May 5, 2005.

Aesthetic Buyers Guide: The Leading Cosmetic Practice Resource, Jan./Feb. 2004, vol. 7, No. I.

(56) References Cited

OTHER PUBLICATIONS

Bollen, CM. et al., "Full- versus partial-mouth disinfection in the treatment of periodontal infections. A pilot study: long-term microbiological observations", J Clin Periodontol Oct. 1996;23(10):960-70 (Abstract).

Bollen, CM. et al., "Full- versus partial-mouth disinfection in the treatment of periodontal infections. A pilot study: long-term microbiological observations", J Clin Periodontol Oct. 1996;23(10):960-70 (Abstract).

Bollen, CM. et al., The effect of a one-stage full-mouth disinfection on different intra-Oral niches. Clinical and microbiological observations•. J Clin Periodontol Jan. 1998;25(1):56-66 (Abstract).

Bollen, CM. et al., "The effect of a one-stage full-mouth disinfection on different intra-oral niches. Clinical and microbiological observations", J Clin Periodontol Jan. 1998;25(1):56-66 (Abstract).

Calderhead, R. Glen, "The Photobiology of LED Phototherapy".

Calder1-Iead, R. Glen, "The Photobiology of LED Phototherapy".

Charakida et al., "Phototherapy in the Treatment of Acne Vulgaris, What is the Role'?", Am. J. Clin. Dermatol 2004: 5(4): 211-216.

Cohen L.R., "What causes bad breath?", University of Toronto; webpage (printed before Nov. 2, 2004).

Cohen LR., "What causes bad breath?", University of Toronto; webpage (printed before Nov. 2, 2004).

Coventry et al. (2000) "ABC of oral health: Periodontal disease" British Medical Journal, 321, 36-39.

De Soete, M. et al .. One-stage full-mouth disinfection. Long-term microbiological results analyzed by checker board DNA-DNA hybridization•, J Periodontol Mar. 2001; 72(3):374-82 (Abstract).

De Soete, M. et al., "One-stage full-mouth disinfection. Long-term microbiological results analyzed by checker board DNA-DNA hybridization", J Periodontol Mar. 2001; 72(3):374-82 (Abstract).

Elman M. et al., "The effective treatment of acne vulgaris by a high-intensity, narrow bank 405-420 nm light source", Cosmetic & Laser Ther 2003; 5: 111-116.

Elman M. et al., The effective treatment of acne vulgaris by a high-intensity, narrow bank 405-420 nm light source•, Cosmetic & Laser Ther 2003; 5: 111-116.

Flow Control Network web page, "Mini Diaphragm Pumps for Precision Dispensing" by Ping Lin, printed Aug. 2, 2005.

Friedberg J.S. et al., "Antibody-Targeted Photolysis Bacteriocidal Effects of Sn (IV) Chlorin e6-0extran-Monoclonal Antibody Conjugates", Annals New York Academy of Sciences 618:383-393, 1991.

Friedberg JS et al., "Antibody-Targeted Photolysis Bacteriocidal Effects of Sn (IV) Chlonn e6-Dextran-Monoclonal Antibody Conjugates", Annals New York Academy of Sciences 618:383-393, 1991.

Greenstein G., Full-mouth therapy versus individual quadrant root planning: a critical commentary, J Periodontol Jul. 2002;73(7):797-812 (Abstract).

Greenstein G., Full-mouth therapy versus individual quadrant root planning: a critical commentary, JPeriodontol Jul. 2002;73(7):797-812 (Abstract).

Guidelines for Limiting Exposure to Time-Varying Electric, Magnetic, and Electromagnetic Fields (up to 300 GHz), International Commission on Non-Ionizing Radiation Protection, ICNIRP Guidelines, Apr. 1998, vol. 7 4, No. 4, pp. 494-522.

Hamblin, M. et al., "Rapid Control of Wound Infections by Targeted Photodynamic Therapy Monitored by In Vivo Bioluminescence Imagining", Photochemistry and Photobiology, 2002, 75(1): 51-57.

Hamblin, M. et al., Rapid Control of Wound Infections by Targeted Photodynamic Therapy Monitored by In Vivo Bioluminescence Imagining•, Photochemistry and Photobiology, 2002, 75(1): 41-57.

Komerik et al. (2003) "In vivo killing of Porphyromonas gingivalis by toluidine blue-mediated photosensitization in an animal model" Antimicrobial Agents and Chemotherapy, 47(3), 932-940.

Krespi, et al. (2005) "Lethal photosensitization of oral pathogens via red-filtered halogen lamp" Oral Diseases, 11(S1), 92-95.

Krespi, et al. (2005) "Lethal photosensitization of oral pathogens via red-filtered halogen larnp" Oral Diseases, 11(S1), 92-95.

Malik, Z. et al., "New Trends in Photobiology (Invited Review) Bactericidal Effects of Photoactivated Porphyrins—An Alternative Approach to Antimicrobial Drugs", Journal of Photochemistry and Photobiology, B: Biology, May 1, 1990}_281-293.

Malik, Z. et al., "New Trends in Photobiology (Invited Review) Bactericidal Effects of Photoactivated Porphyrins•An Alternative Approach to Antimicrobial Drugs", Journal of Photochemistry and Photobiology, B: Biology, 5 J.19901_281-293.

Matevski D. et al., "Lethal photosensitization of periodontal pathogens by a red-filtered Xenon lamp in invitro", J. Periodont. Res. 2003, 38:428-435.

Matevski D. et al., "Lethal photosensitization of periodontal pathogens by a red-filtered Xenon lamp in invitro", JPeriodont. Res. 2003, 38:428-435.

Matevski D. et al., Sensitivity of Porphyromonas gingivalis to Light-Activated Toluidine Blue o•. University of Toronto, Faculty of Denistry; Slide presentation (presented before Nov. 15, 2002).

Matevski D. et al., "Sensitivity of Porphyromonas gingivalis to Light-Activated Toluidine Blue O", University of Toronto, Faculty of Denistry; Slide presentation (presented before Nov. 15, 2002).

Meisel et al. (2005) Photodynamic therapy for periodontal diseases: State of the are• J. Photochem. Photobiol., 79, 159-170.

Meisel etal. (2005) "Photodynamic therapy for periodontal diseases: State of the are" J. Photochem. Photobiol., 79, 159-170.

Mongardini, C. et al., One stage full- versus partial-mouth disinfection in the treatment of chronic adult or generalized early-0nset periodontitis. I. Long-tenn clinical observations•, J Periodontol Jun. 1999;70(6):632-45 _[Abstrac!)_.

Mongardini, C. et al., "One stage full- versus partial-mouth disinfection in the treatment of chronic adult or generalized early-onset periodontitis. I. Long-term clinical observations", J Periodontol Jun. 1999;70(6):632-45 1Abstrac!2._.

Morton C.A. et al., An open study to determine the efficacy of blue light in the treatment of mild to moderate acne: preliminary data (publication status unknown).

Nakano et al. (2002) "Correlation between oral malodor and periodontal bacteria" Microbes Infect., 4(6), 679-683.

Nakano et al. (2002) "Correlation between oral malodor and periodontal bacteria" Microbes Infect., 4(6). 679-683.

Ondine Biopharma web page—printed Oct. 15, 2002.

Papageorgiou ct al., "Phototherapy with blue (415 nm) and red (660 nm) light in the treatment of acne vulgaris", British Journal of Dermatology 2000: 142: 973-978.

Pharmaceutical description, Levulan® Kerastick *arninolevulinic acid I-IC!) for Topical Solution, 20'X.

Pharmaceutical description, Levulan® Kerastick •aminolevulinic acid HCI) for Topical Solution, 20%.

Quirynen, M. et al. Fuli- vs. partial-mouth disinfection in the treatment of periodontal infections: short-tennclinical and microbiological observations•. J Dent Res Aug. 1995;74(8):1459-67 (Abstract).

Quirynen, M. et al. "Full- vs. partial-mouth disinfection in the treatment of periodontal infections: short-term clinical and microbiological observations", J Dent Res Aug. 1995;74(8):1459-67 (Abstract).

Quirynen, M. et al., "One stage full- versus partial-mouth disinfection in the treatment of chronic adult or generalized early-onset periodontitis. II. Long-term impact on microbial load", J Periodontol Jun. 1999:70(6):646-56 (Abstract).

Quirynen, M. et al., "The effect of a 1-stage full-mouth disinfection on oral malodor and microbial colonization of the tongue in periodontitis. A pilot study", J Periodontol Mar. 1998;69(3):374-82 (Abstract).

Quirynen, M. et al., "The intra-oral translocation of periodontopathogens jeopardises the outcome of periodontal therapy", Journal of Clincial Periodontology, Jun. 2001, vol. 28, Issue 6, p. 499 (Abstract).

Quirynen, M. et al., The role of chlorhexidine in the one-stage full-mouth disinfection treatment of patients with advanced adult periodontitis. Long-term clinical and microbiological observations•. J Clin Periodontol 2000 A1.IQ;27.{fil:579-89 J_Abstrac!)_.

Quirynen, M. et al., "The role of chlorhexidine in the one-stage full-mouth disinfection treatment of patients with advanced adult periodontitis. Long-term clinical and microbiological observations", J Clin Periodontol 2000 A1?JL2~579-89 J_Abstrac_!).

(56) References Cited

OTHER PUBLICATIONS

Quirynen. M. et al., "One stage full- versus partial-mouth disinfection in the treatment of chronic adult or generalized early-onset periodontitis. II. Long-term impact on microbial load", J Periodontol Jun. 1999;70(6):646-56 J_Abstrac!2._.

Sanz et al. (2001) "Fundamentals of breath malodour" Journal of Contemporary Dental Practice, 2(4 ), 1-13.

Sanz et al. (2001) "Fundamentals of breath malodour" Journal of Contemporary Dental Practice, 2(4), 1-13.

Sarkar et al. (1993) "Lethal photosensitization of bacteria in subgingival plaque from patients with chronic periodontitis" J. Periodont. Res , 28, 204-21 O.

Sarkar et al. (1993) "Lethal photosensitization of bacteria in subgingival plaque from patients with chronic periodontis" J. Periodont. Res., 28, 204-210.

Search results from Delphion web site, dated Nov. 22, 2005.

Skin91 I .com web page regarding Peter Thomas Roth Clinical Acne Medication, acne treatment—Benzoyl Peroxide 5% pbp5, printed Apr. 19, 2005.

Soukos et al. (1998) "Targeted antimicrobial photochemotherapy", Antimicrobial Agents and Chemotherapy 42( 10 ), 2595-2601.

Soukos et al. (1998) "Targeted antimicrobial photochemotherapy", Antimicrobial Agents and Chemotherapy 42(10), 2595-2601.

Spire Awarded Contract for Ear Surgery Laser—Press Release Aug. 23, 2002.

Temperatures.com web page, "Thermistor Temperature Sensors," printed Aug. 2, 200.

Temperatures.corn web page, "Thermistor Temperature Sensors," printed Aug. 2, 200.

Vandekerckhove, BN. et al., "Full- versus partial-mouth disinfection in the treatment of periodontal infections. Long-term clinical observations of a pilot study", J Periodontol Dec. 1996;67(12):1251-9 (Abstract).

Vandekerckhove, BN. et al.. "Full- versus partial-mouth disinfection in the treatment of periodontal infections. Long-term clinical observations of a pilot study", J Periodontol Dec. 1996;67(12):1251-9 (Abstract).

Wainwright M., Photodynamic antimicrobial chemotherapy (PACT), Journal of Antimicrobial Chemotherapy (1998) 42, 13-28.

Wilson (2005) "Lethal photosensitisation of oral bacteria and its potential application in the photodynamic therapy of oral infection" Photochem. Photobiol. Sci .. 3, 412-418.

Wilson (2005) "Lethal photosensitisation of oral bacteria and its potential application in the photodynamic therapy of oral infection" Photochem. Photobiol. Sci., 3, 412-418.

Wilson et al. (1995) "Bacteria in supragingival plaque samples can be killed by low-power laser light in the presence of a photosensitizer" J. Appl. Bacteriol .. 78, 569-574.

Wilson et al. (1995) "Bacteria in supragingival plaque samples can be killed by low-power laser light in the presence of a photosensitizer" J. Appl. Bacteriol., 78, 569-574.

Wood, et al. (1999) "An in vitro study of the use of photodynamic therapy for the treatment of natural oral plaque biofilms formed in vivo" J. Photochem. Photogiol. B: Biol .. 50, 1-7.

Wood, et al. (1999) "An in vitro study of the use of photodynamic therapy for the treatment of natural oral plaque biofilms formed in vivo" J. Photochem. Photogiol. B: Biol., 50, 1-7.

www.lightbioscience.com web page, Gentle Waves Cosmcceuticals, printed Jul. 29, 200.

www.lightbioscience.com web page, Gentle Waves LED Photomodulation Fact Sheet, printed Jul. 29, 2005.

www.lightbioscience.com web page, GentleWaves Cosmeceuticals, printed Jul. 29, 200.

www.lightbioscience.com web page, GentleWaves LED Photomodulation Fact Sheet, printed Jul. 29, 2005.

PCT/IL11/00630 International Search Report.
PCT/IL11/00256 International Search Report.
PCT/IL11/00170 International Search Report.
PCT/IL10/00751 International Search Report.
PCT/IL09/00693 International Search Report.

* cited by examiner

DETAIL I-I

RF ELECTRODE FOR AESTHETIC AND BODY SHAPING DEVICES AND METHOD OF USING SAME

CROSS-REFERENCE TO RELATED APPLICATIONS

This application is related to the U.S. Provisional Application for Patent assigned Ser. No. 61/081,110, filed Jul. 16, 2008 which is hereby incorporated by reference.

TECHNICAL FIELD

The device and method relate to the field of aesthetic treatment and body shaping devices and more specifically to the use of a cooled RF electrode in aesthetic and body shaping devices.

BACKGROUND

The practice of using heat energy for aesthetic treatment and body shaping is known in the art. Heating of the skin and the underlying tissues over certain temperatures or temperature ranges results in tissue shrinkage and produces a desired aesthetic effect. The application of RF energy is one of the methods of heating the skin and underlying tissues.

Aesthetic and/or body shaping treatment is administered using an applicator coupled with an RF electrode or energy delivery device connected to a source of RF. The electrode typically has an RF energy delivery surface. The surface is applied to the surface of the skin and couples to it the RF energy, which produces heat transferred into the skin and underlying subcutaneous tissues to create the desired effect that may be tissue shrinkage, wrinkle removal, collagen distraction, acne removal, etc. The heat induced in the skin and underlying subcutaneous tissues by the RF energy is not distributed in a balanced way across the electrode surface coupled with the skin, especially in the places where the skin does not form a good contact across the whole surface of the electrode. Segments of skin being in contact with the electrode surface receive a higher dose of RF energy and form so called "hot spots". In many situations, the temperature of the hot spots is high enough to damage the skin. In order to avoid the skin overheating, and in some cases skin burns, the whole electrode is cooled by a cooling fluid or other type of coolant. The author of the present method has theoretically and experimentally established that in addition to hot spots a larger amount of energy concentrates along the periphery of the electrode energy delivery surface and more specifically at the corners and edges of the electrode. In order to improve heat distribution over the skin surface that is coupled with the electrode, electrodes with rounded edges and corners were produced and tested. The rounded edges and corners have, to some extent, mitigated the heating effect, but the skin segments that are adjacent to the electrodes are still excessively heated by the RF.

Because of this uneven RF energy distribution across the electrode, achieving an effective treatment RF energy level across the electrode and in particular at the center portion of the electrode energy delivery surface, results in excessive heating at the energy delivery surface periphery and corners. This causes undesired pain and possible damage to the skin and underlying subcutaneous tissue coupled with these peripheral areas and corners. This phenomenon precludes achieving a sufficiently high, but safe level of energy that can be coupled to the skin through the RF electrode.

BRIEF SUMMARY

The present energy delivery device or electrode and method provide a solution for the overheating of the skin and underlying subcutaneous tissue coupled with the peripheral areas of the RF electrode energy delivery surface. The electrode energy delivery surface is segmented and the peripheral segments cooled thus creating a more balanced distribution of heat over the RF electrode energy delivery surface coupled with the skin. Advantageously, this enables safe and effective aesthetic procedures or treatment and body shaping. The central segment of the electrode may optionally be heated to reduce the treatment energy losses.

GLOSSARY

The term "monopolar configuration" as used in the present disclosure means a configuration consisting of an active treatment electrode and a passive one, which acts as the grounding electrode. Typically the electrodes are different in size, with the passive electrode being larger than the active electrode, and located at a distance between them. RF induced current affects the tissue area/volume that is proximate to the active electrode.

The term "bipolar configuration" as used in the present disclosure means that the current passes between two identical electrodes located a short distance apart from each other. They are applied to the area/volume of skin/tissue to be treated and the propagation of the current is limited to the area/volume between the electrodes themselves.

The term "coolant" or "temperature control element" as used in the present text means water, specially prepared mixtures of fluids, and such cooling elements like solid state thermoelectric cooling elements.

The term "temperature stabilizing element" as used in the present text means an element capable of heating or cooling the element to which it is attached. Such element may be a heating element, a switchable cooling/heating fluid conduit and other elements capable of performing the temperature stabilizing task.

The term "skin" as used in the present disclosure means the outer skin layers such as stratum corneum, dermis, epidermis, etc.

The terms "tissue", as used in the present disclosure means the deeper skin layers such as adipose tissue or muscle.

BRIEF LIST OF DRAWING

The method and the device are particularly pointed out and distinctly claimed in the concluding portion of the specification. The method and the device, however, both as to organization and method of operation, may best be understood by reference to the following detailed description when read with the accompanying drawings, in which like reference characters refer to the same parts throughout the different views. The drawings are not necessarily to scale, emphasis instead being placed upon illustrating the principles of the method.

DETAILED DESCRIPTION OF EXEMPLARY EMBODIMENTS

In the following detailed description, reference is made to the accompanying drawings that form a part hereof and wherein like reference numerals denote like elements through the several views.

Figure 1A:
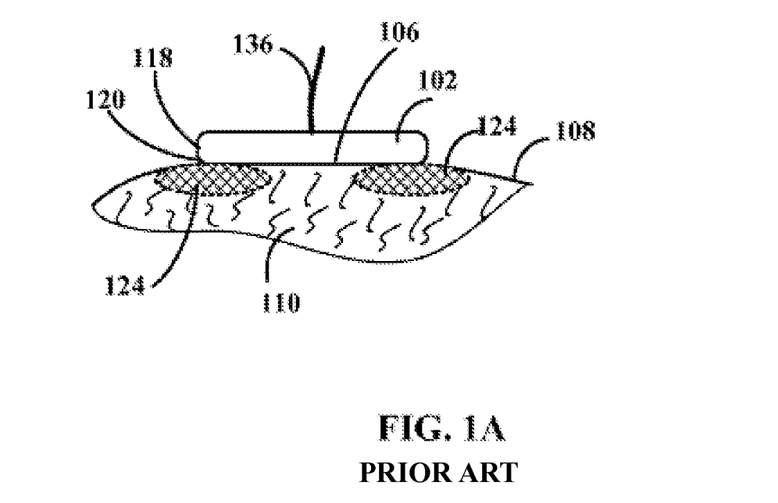
FIGS. 1A and 1B are schematic illustrations of the skin overheating effect by the periphery of a conventional RF electrode.
Figure 1B:
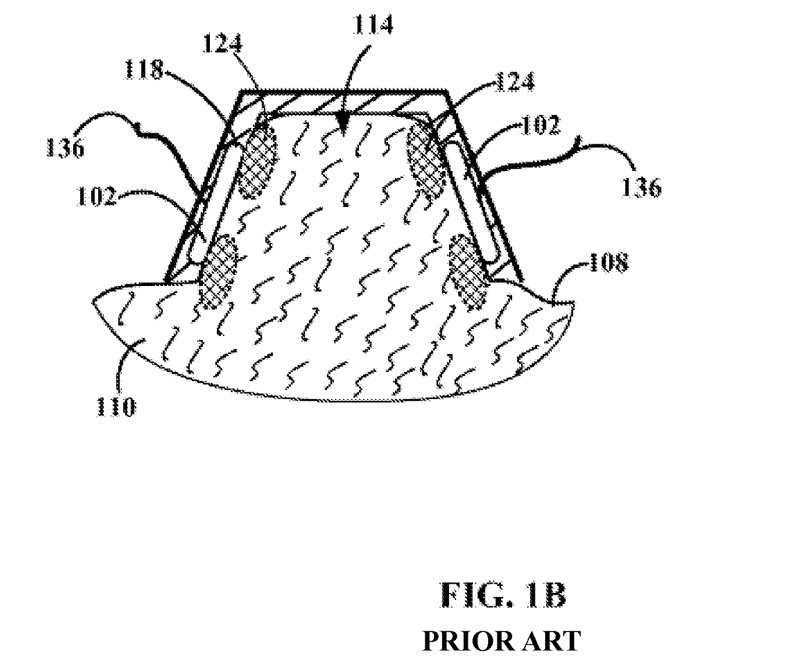

FIGS. 1A and 1B are schematic illustrations of the skin overheating effect by the periphery of a conventional (one of a pair) RF electrode. FIG. 1A schematically illustrates the skin overheating effect caused by a non-segmented RF electrode 102. Electrode 102 has a single-segment energy delivery surface 106 coupled through the surface of skin 108 to a volume of underlying subcutaneous tissue 110. For the simplicity of explanation the second or return electrode is not shown. Electrode 102 is applied to a segment of skin 108 or to a skin protrusion 114 (see FIG. 1B) formed by any known protrusion forming methods. For example, the United States Provisional Application for Patent assigned Ser. No 61/081, 110 and assigned to the same assignee as this present disclosure and incorporated herein in its entirety, discloses a method of forming a skin protrusion. In the current embodiment, the volume of skin and subcutaneous tissue 108 forming the protrusion is about 30 to 40 mm wide and 10 to 30 mm deep.

As indicated above, the author of the present disclosure has discovered that despite the fact that electrode 102 has rounded peripheral edges and corners, the skin and tissue that is immediate adjacent to these edges and corners is affected by higher RF energy density accumulated in the periphery 118 of electrode 102 and primarily in the corners 120. This phenomenon causes areas 124 of skin 102 and underlying subcutaneous tissue 110 to overheat, which causes undesired pain and sometimes irreparable damage to the skin and underlying subcutaneous tissue in these areas 124. In order to reduce the adverse effects of the skin overheating, the electrodes may be cooled by a cooling fluid or other cooling techniques known in the art. This however, increases energy losses, since a part of the energy heating the skin is transferred to the electrode being in contact with the treated skin segment and reduces the treatment efficiency. Numeral 136 marks cables connecting the electrodes with an RF power supply.

The edge and adjacent to the edge skin overheating phenomenon precludes achieving a safe level of energy that can be coupled through the RF electrode 102 energy delivery surface 106 and that will still be effective for aesthetic treatment or body shaping treatment. Applying a coolant only to the periphery 118 and corners 120 will cool areas 124 and will provide a balanced distribution of heat over the energy delivery surface segment 106 allowing for safe and effective skin and tissue RF treatment. This may be achieved by the employment of a segmented RF electrode.

Figure 2A:
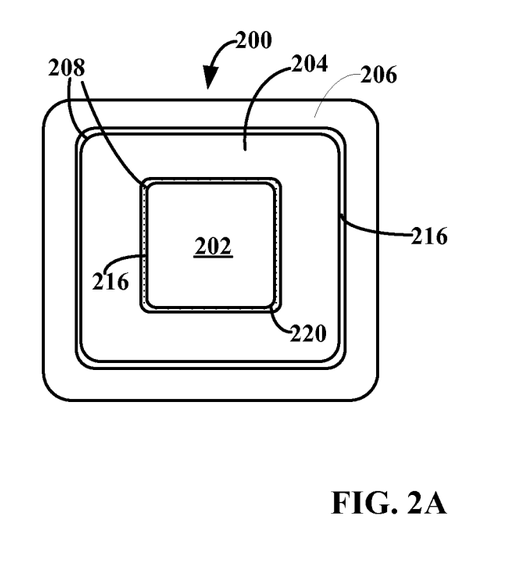
FIG. 2A is a schematic frontal view of an exemplary embodiment of the segmented RF electrode energy delivery surface.
Figure 2B:
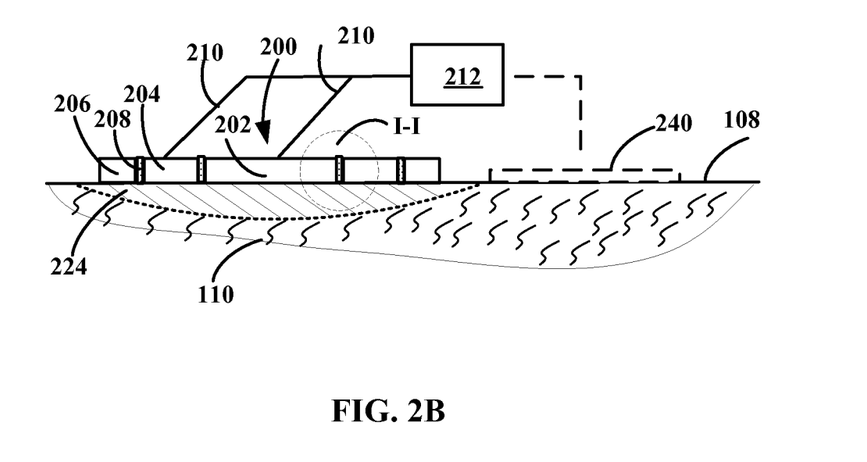
FIG. 2B is a cross-sectional view of an exemplary embodiment of the segmented RF electrode energy delivery surface.
Figure 2C:
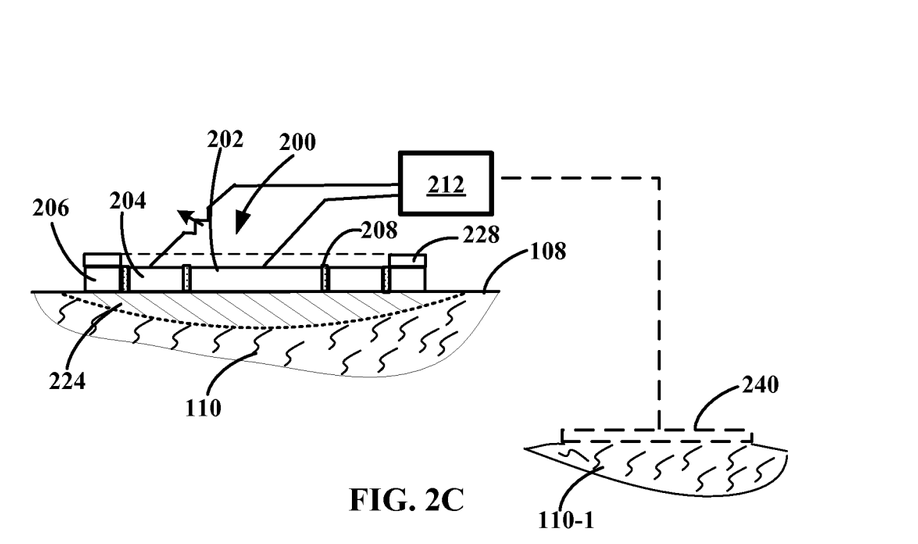
FIG. 2C is a cross-sectional view of another exemplary embodiment of the segmented RF electrode energy delivery surface.

FIGS. 2A-2C illustrate an exemplary embodiment of an energy delivery system with FIG. 2A providing a frontal view and FIGS. 2B-2C providing cross-sectional views of the exemplary embodiment of an energy delivery surface segments of a segmented RF electrode 200. The illustration depicts a central segment 202 having a size of about 15 to 35 mm wide and two peripheral segments 204 and 206 arranged along the perimeter of segment 202. Thermal and electrical insulation 208 between central segment 202 and peripheral segments 204 and 206 is also illustrated. Typically, the thermal and electrical insulation is about 0.5-1.0 mm wide. In the current embodiment of the segmented RF electrode, the peripheral segments 204 and 206 are about 2 to 10 mm wide and are made of a thermally conductive material. Electrode 204 is made of electrically conductive material and electrode 206 is made of electrically insulating material. In particular, the segments 206 of the electrodes were made of materials selected from a group consisting of metal oxides or Ceramics. Aluminum nitride, Boron nitride, and similar are examples of such materials. Electrode 200 is shown as a square electrode, but it may be of round, rectangular, elliptical and other suitable shapes. Accordingly, electrodes 204 and 206 may have a similar shape following the perimeter of the central electrode segment. Electrodes 204 and 206 may have uniform width or sections of different width.

FIG. 2B further illustrates an RF energy source 212 connected and providing RF energy to central electrode segment 202 and peripheral electrode segment 204. In the current embodiment the central electrode segment 202 and peripheral electrode segment or temperature control element 204 are connected in parallel over line 210 to the RF energy source 212, whereas peripheral segment 206 is an insulated element and thus, is not connected to the RF energy source 212.

In another embodiment of the segmented RF electrode illustrated in FIG. 2C, the central segment 202 and peripheral segment 204 are independently connected to the RF energy source 212 and are configured to create a controllable variable potential gradient between them. FIGS. 2B and 2C show a return electrode 240 located proximal to the electrode 202 in a bi-polar configuration and remote from the electrode 202 in a mono-polar configuration. Numeral 110-1 schematically illustrates the segment of skin to which the return electrode is applied in the mono-polar configuration.

The peripheral segments 204 and 206 are cooled, diminishing the overheating effect of central segment 202 peripheries 216 and corners 220, cooling the skin 108 and underlying subcutaneous tissue 110 to a temperature at least equal to or lower than the temperature of skin coupled to the central segment 202 and effecting a more balanced heat distribution and penetration. The temperature of the central segment 202 may be stabilized by a temperature stabilizing element (See FIGS. 5A-5B) and maintained at 35-42 degrees Celsius reducing the treatment energy losses.

The central segment 202 of the electrode 200 may even have a heater keeping it through the stand by period at a temperature of about 35 to 42 degrees Celsius, which is higher than the temperature of the peripheral segments 204 and 206, shortening the treatment duration and reducing energy waste. Alternatively, the heater may accelerate central segment 202 heating immediately with the beginning of the skin or tissue treatment.

Hatched area 224 depicts the level of heat penetration into the skin 108 and underlying subcutaneous tissue 110. The cooling of the peripheral segments 204 and 206 dampens the overheating effect of the perimeter 216 and corners 220 (see FIG. 2A) of central segment 202 and contributes to a more balanced and safe distribution and penetration of heat into the skin 108 and underlying subcutaneous tissue 110.

In another embodiment, the temperature control element is a thermoelectric cooler 228 that cools directly one or more of the peripheral segments of electrode 200 (see FIG. 2C).

Figure 3:
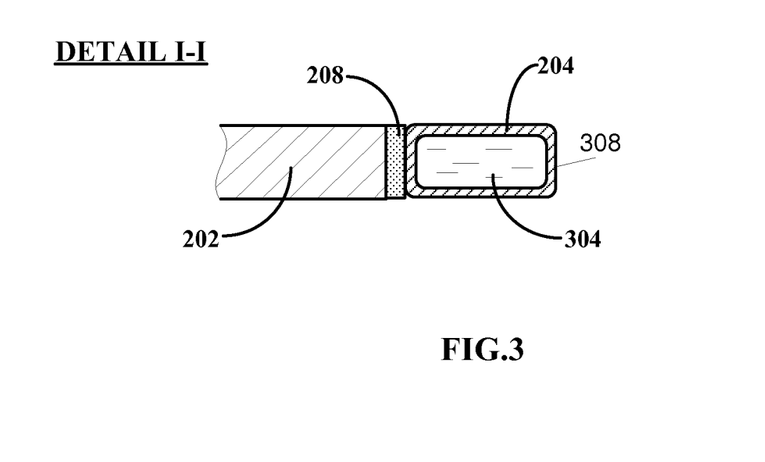
FIG. 3 is an enlargement of the section I-I marked by a broken-line circle in FIG. 2B demonstrating a temperature control element of the segmented electrode.

FIG. 3, is an enlarged section of FIG. 2B, it illustrates an exemplary embodiment of a temperature control element within peripheral energy delivery surface segment 204 thermal and electrical insulation 208 and central electrode segment 202. The temperature control element comprises a coolant 304 connected to a coolant source (not shown) flowing through a coolant carrying conduit 308, within peripheral segment 204. Peripheral segment 206 has a structure similar to segment 204, although the size of the coolant carrying conduit may be different. The coolant 304 may be water, alcohol, specially prepared fluids including material enhancing heat exchange and even cryogenic fluids.

Figure 4:
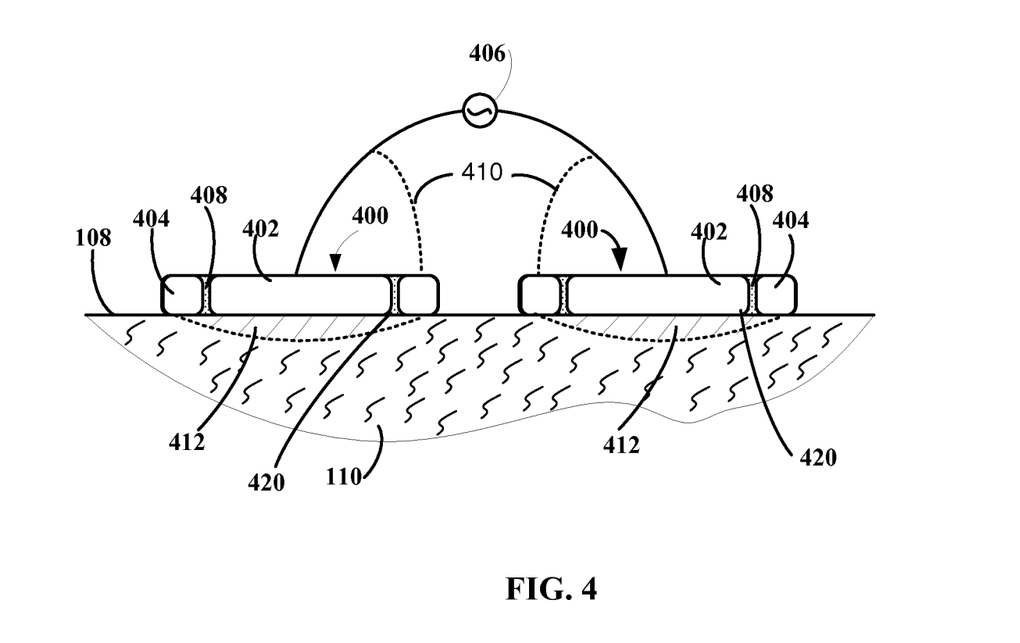
FIG. 4 is a schematic illustration of another embodiment of the energy delivery surface of an RF applying segmented electrode.

FIG. 4 illustrates another embodiment of use of a segmented RF electrode. Two segmented RF electrodes 400 are placed on a surface of skin 108. Each segmented RF electrode 400 is comprised of a central segment 402, a single peripheral segment 404 surrounding the perimeter of the central segment 402 and thermal and electrical insulation 408 between the central segment 402 and the peripheral segment 404.

The central segment 402 of each of the electrodes is connected to an RF source 406, whereas the RF energy source connection 410 to peripheral segment 404 is a floating connection. The peripheral segment 404 as explained above is cooled, so that in the course of treating a segment of skin, the temperature of the central segment of the energy delivery surface may be higher than the temperature of the peripheral segment.

Area 412 depicts schematically the level of heat penetration into the skin 108 and underlying subcutaneous tissue 110. The cooling of the peripheral segment 404 dampens the overheating effect of the perimeter and corners 420 of central segment 402 and contributes to a more balanced and safe distribution and penetration of heat into the skin 108 and underlying subcutaneous tissue 110.

It has been experimentally established that with the beginning of the treatment, a large portion of the RF energy heating the skin is transferred by heat conduction from the skin to the electrode. Actually, the treatment becomes effective only when a thermal equilibrium between the skin and electrode temperature is reached. The central segment of the present electrode may be heated and maintained at a temperature of 35-42 degrees Celsius, which is a typical treatment temperature, reducing the heat from skin to the electrode transfer and minimizing the treatment energy losses. The heating may be performed by including a heating element in the central segment of the electrode. The heating element may be a resistive heater or a fluid conduit into which a warm heating fluid is pumped. In case of need, the fluid supply may be switched to a cooling fluid and cool the central segment of the electrode. Alternatively, a thermoelectric element driven by a voltage of one polarity for heating, and reverse polarity for cooling may be used for heating and or cooling of the central segment of the electrode.

Figure 5A:
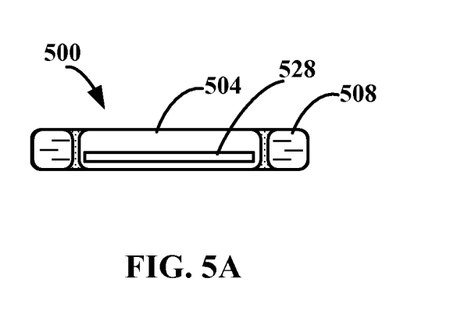
FIGS. 5A and 5B are cross-sectional views of additional exemplary embodiments of the segmented RF electrode.
Figure 5B:
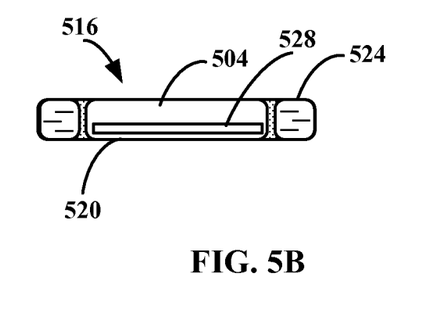

FIGS. 5A and 5B are cross-sectional views of additional exemplary embodiments of the segmented RF electrode. FIG. 5A illustrates a configuration where electrode 500 includes a central segment 504 and a peripheral segment 508. Both segments are driven by the same or different RF energies. Central segment 504 includes a temperature stabilizing element, which in this particular case is a heating element 528 configured to be operable for heating and maintaining the temperature of the central segment 504 of the electrode 500 through a stand-by period at a temperature of about 35 to 42 degrees Celsius, which is higher than the temperature of the peripheral segments 204 and 206, shortening the treatment duration and reducing energy waste. Alternatively, the heater may accelerate central segment 504 heating immediately with the beginning of the skin or tissue treatment. FIG. 5B illustrates a configuration where electrode 516 includes a central segment 520, a peripheral segment 524, and a temperature stabilizing element 528. Segment 520 is driven by the RF energy, where segment 524 is made of insulating material.

Figure 6:
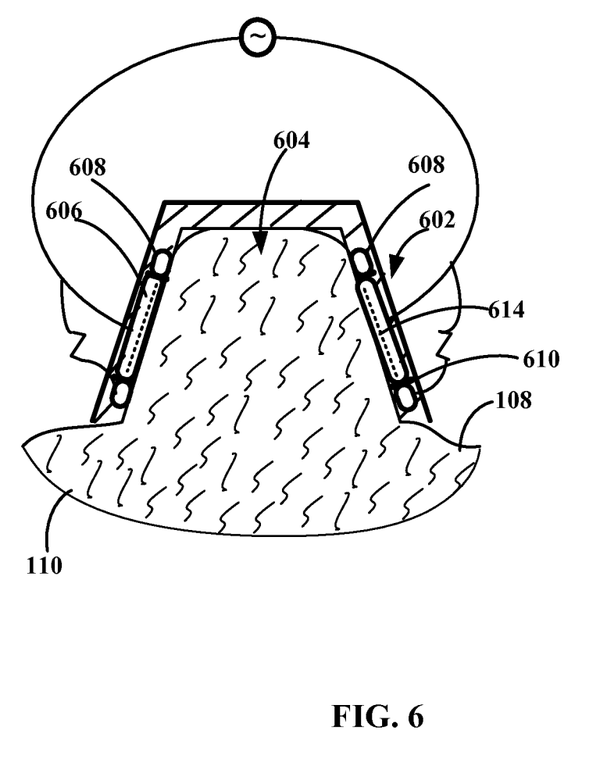
FIG. 6 is a cross-sectional view of a further exemplary embodiment of the segmented RF electrode applied to a skin protrusion.

FIG. 6 is a cross-sectional view of a further exemplary embodiment of the segmented RF electrode applied to a skin protrusion. Electrode 602 is applied to a skin protrusion 604 formed by any known protrusion forming method. Electrode 602 includes a central segment 606 and one peripheral segment 608 arranged along the perimeter of segment 606. Thermal and electrical insulation 610 between central segment 606 and peripheral segment 608 and temperature stabilizing element 614 (shown in phantom lines) are also illustrated. In some embodiments, there may be two or more peripheral segments. The central segment may be 20 to 30 mm large and the peripheral segments may be about 2 to 10 mm wide. The peripheral segments are made of a thermally conductive material. Depending on a number of peripheral segments, some of them may be made in addition to thermally conductive material of electrically conductive material and some of them may be made of electrically insulating material.

In use the present RF electrode or energy delivery device would be coupled to an applicator and used for different aesthetic and other skin treatment procedures.

The presented device and method provide a solution for the undesired overheating of the skin being in contact with the periphery of the RF electrode energy delivery surface and enable achieving a more balanced distribution of heat. This also enables increasing the RF energy levels emitted by the RF electrode, to levels safe and effective for treatment, without overheating the skin and underlying subcutaneous tissues.

The various embodiments that have been illustrated, as well as combinations thereof and variations thereof operate to alleviate, or at a minimum reduce an adverse affect that arises in the treatment of skin and tissue utilizing electrodes. Because of the tendency for increased RF energy to emanate from the periphery and corners of an electrode (even if rounded or contoured to over come the phenomenon), when applying an amount of energy necessary to properly treat a particular skin segment, skin areas proximate to the periphery and corners of the probe are heated to a higher temperature and can be damaged. Lowering the RF energy in the electrode helps prevent skin damage but also diminishes the overall effect or efficiency of the treatment. By utilizing multi-segmented probes, the effect of increased energy at the corners and periphery can be alleviated or reduced. Further, by selecting peripheral segments that can be further controlled, such as cooling, the temperature delivered to the skin at the corners and periphery of the main segment of the probe can be controlled and reduced. Further, by including the ability to increase the heat of the main segment by the introduction of a temperature stabilizing element, increased energy can be delivered to the treated skin segment without overheating the skin area proximate to the corners and/or periphery of the probe.

A number of embodiments have been described. Nevertheless, it will be understood that various modifications may be made without departing from the spirit and scope of the method and electrode structure. Accordingly, other embodiments are within the scope of the following claims.

What is claimed is:

1. A skin and subcutaneous heating RF electrode for aesthetic and body shaping devices, the RF electrode comprising:
    a segmented energy delivery surface having one central segment and at least a first peripheral segment arranged along the perimeter of the central segment and thermally and electrically insulated therefrom and wherein the at first peripheral segment defines a conduit;
    wherein the first peripheral segment surrounds the central segment and is constructed of an electrically conductive material;
    a coolant fluid enclosed in the conduit;
    a source of RF energy connected to both the central segment and the first peripheral segment;
    a second peripheral segment constructed of an electrically insulating material arranged along a perimeter of the first peripheral segment and surrounding the first peripheral segment;
    wherein the first peripheral segment and second peripheral segment are separated by thermal and electrical insulation.

2. The RF electrode according to claim 1, further comprising thermal and electrical insulation between the central segment and the first peripheral segment.

3. The RF electrode according to claim 1, wherein the first peripheral segment and second peripheral segment are both made of thermally conductive materials.

4. The RF electrode according to claim 1, wherein a thermoelectric cooler is operably connected to and cools the at least second peripheral segment and the source of RF energy is connected in parallel to the first peripheral segment.

5. The RF electrode according to claim 1, wherein the RF energy source is connected in parallel to the central segment and to the first peripheral segment.

6. The RF electrode according to claim 1, wherein the RF energy source is independently connected to the central segment and to the first peripheral segment and configured to create a controllable variable electric potential gradient between the central segment and to the first peripheral segment.

7. The RF electrode according to claim 1, wherein the central segment further comprises a temperature stabilizing element.

8. The RF electrode according to claim 7, wherein the temperature stabilizing element maintains the temperature of the central segment at 35-42 degrees Celsius.

9. The RF electrode according to claim 7, wherein the temperature stabilizing element is operable to heat or cool the central segment and the fluid coolant is operable to cool the at least one peripheral segment and the perimeter of the central segment.

10. The RF electrode according to claim 1, operably coupled to an applicator.

11. The RF electrode according to claim 1, wherein the at least one peripheral segment is made of a material selected from the group consisting of metal oxides and ceramics.

12. The RF electrode according to claim 1, wherein the at least first peripheral segment is operative to cool the peripheries and corners of the central segment.

13. An applicator for aesthetic skin treatment, the applicator comprising:
    an RF electrode with a segmented energy delivery surface having one central segment and at least two peripheral segments, the at least two peripheral segments arranged peripherally from and surrounding a perimeter of the central segment and wherein the central segment and the at least two peripheral segments are thermally and electrically insulated from one another;
    a conduit defined by at least a first peripheral segment of the at least two peripheral segments and wherein a coolant fluid is enclosed by the conduit;
    wherein the first peripheral segment is constructed of an electrically conductive material;
    a source of RF energy connected to at least the central segment and the first peripheral segment;
    wherein a second peripheral segment of the at least to peripheral segments is arranged peripherally from and surrounding a perimeter of the first peripheral segment and is constructed of an electrically insulating material;
    and a temperature stabilizing element connected to the central segment.

14. The applicator according to claim 13, wherein the temperature stabilizing element is configured to maintain the temperature of the central segment in a range of 35-42 degrees Celsius.

15. The RF electrode according to claim 14, wherein the temperature stabilizing element is operable to heat or cool the central segment and the coolant fluid is operable to cool the at least one of the at least two peripheral segment and the perimeter of the central segment.

* * * * *